US008629769B2

(12) United States Patent
Bruce (10) Patent No.: US 8,629,769 B2
(45) Date of Patent: Jan. 14, 2014

(54) METHOD AND SYSTEM FOR COMMUNICATION BETWEEN WIRELESS DEVICES

(75) Inventor: Robert Bruce, Beaverton, OR (US)

(73) Assignee: iSense Corporation, Wilsonville, OR (US)

( * ) Notice: Subject to any disclaimer, the term of this patent is extended or adjusted under 35 U.S.C. 154(b) by 1050 days.

(21) Appl. No.: 12/549,005

(22) Filed: Aug. 27, 2009

(65) Prior Publication Data

US 2010/0052899 A1 Mar. 4, 2010

Related U.S. Application Data

(60) Provisional application No. 61/092,717, filed on Aug. 28, 2008.

(51) Int. Cl.
*G08B 1/08* (2006.01)
(52) U.S. Cl.
USPC ............... 340/539.12; 340/10.1; 370/329; 370/254; 370/348
(58) Field of Classification Search
USPC .............. 340/539.12, 10.1; 455/41.2, 450; 370/329, 254, 348
See application file for complete search history.

(56) References Cited

U.S. PATENT DOCUMENTS

| | | |
|---|---|---|
| 4,952,928 A | 8/1990 | Carroll et al. |
| 5,137,020 A | 8/1992 | Wayne et al. |
| 5,239,275 A | 8/1993 | Leitch |
| 5,381,798 A | 1/1995 | Burrows |
| 5,400,794 A | 3/1995 | Gorman |
| 5,476,488 A | 12/1995 | Morgan et al. |
| 5,507,288 A | 4/1996 | Böcker et al. |
| 5,509,027 A | 4/1996 | Vook et al. |
| 5,538,007 A | 7/1996 | Gorman |
| 5,581,576 A | 12/1996 | Lanzetta et al. |

(Continued)

FOREIGN PATENT DOCUMENTS

| | | |
|---|---|---|
| EP | 1151759 | 11/2001 |
| JP | 10-023533 | 1/1998 |

(Continued)

OTHER PUBLICATIONS

Medical Devices WG: "Multi-Channel Adaptation Protocol;" XP7921778, Retrieved from the Internet: https://www.bluetooth.org/DocMan/handlers/DownloadDoc.ashx?doc_id=119995; retrieved on Apr. 15, 2013.

(Continued)

*Primary Examiner* — Hoi Lau
(74) *Attorney, Agent, or Firm* — Schwabe, Williamson & Wyatt, P.C.

(57) ABSTRACT

Systems and techniques for command communication between wireless devices are described. In one implementation, a data gathering device (such as a continuous glucose monitor) and a monitoring/control device, which communicate data samples through a frequency hopping protocol, utilize a dedicated command frequency for the transmission of non-data instructions and acknowledgements. A command mode is described where the command frequency is regularly listened to by a device to determine if pairing or other instructions are being sent. In another example, when communications are disrupted or corrupted, the devices revert to using the command frequency in order to reacquire a paired link between the devices. The command frequency is also used for a flight mode, where the data-acquisition device goes into a low-, or no-power transmission mode and remains in the mode, storing sampled data, until instructed to leave the flight mode over the command frequency.

26 Claims, 7 Drawing Sheets

(56) References Cited

U.S. PATENT DOCUMENTS

| | | |
|---|---|---|
| 5,617,871 A | 4/1997 | Burrows |
| 5,790,533 A | 8/1998 | Burke et al. |
| 5,793,261 A | 8/1998 | Boling |
| 5,913,827 A | 6/1999 | Gorman |
| 5,987,352 A | 11/1999 | Klein et al. |
| 6,067,474 A | 5/2000 | Schulman et al. |
| 6,093,146 A | 7/2000 | Filangeri |
| 6,200,265 B1 | 3/2001 | Walsh et al. |
| 6,225,901 B1 | 5/2001 | Kail, IV |
| 6,289,238 B1 | 9/2001 | Besson et al. |
| 6,384,728 B1 | 5/2002 | Kanor et al. |
| 6,441,747 B1 | 8/2002 | Khair et al. |
| 6,450,172 B1 | 9/2002 | Hartlaub et al. |
| 6,477,424 B1 | 11/2002 | Thompson et al. |
| 6,544,174 B2 | 4/2003 | West et al. |
| 6,546,268 B1 | 4/2003 | Ishikawa et al. |
| 6,558,320 B1 | 5/2003 | Causey, III et al. |
| 6,560,471 B1 | 5/2003 | Heller |
| 6,561,975 B1 | 5/2003 | Pool et al. |
| 6,564,105 B2 | 5/2003 | Starkweather et al. |
| 6,577,893 B1 | 6/2003 | Besson |
| 6,577,899 B2 | 6/2003 | Lebel et al. |
| 6,579,231 B1 | 6/2003 | Phipps |
| 6,659,948 B2 | 12/2003 | Lebel et al. |
| 6,687,546 B2 | 2/2004 | Lebel et al. |
| 6,718,177 B1 | 4/2004 | Comer et al. |
| 6,720,887 B1 | 4/2004 | Zunti |
| 6,738,671 B2 | 5/2004 | Christophersom et al. |
| 6,758,810 B2 | 7/2004 | Lebel et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,893,395 B1 | 5/2005 | Kraus et al. |
| 6,940,403 B2 | 9/2005 | Kail, IV |
| 6,958,705 B2 | 10/2005 | Lebel et al. |
| 6,993,393 B2 | 1/2006 | Von Arx et al. |
| 7,022,072 B2 | 4/2006 | Fox et al. |
| 7,044,911 B2 | 5/2006 | Drinan et al. |
| 7,088,233 B2 | 8/2006 | Menard |
| 7,098,803 B2 | 8/2006 | Mann et al. |
| 7,110,783 B2 | 9/2006 | Bahl et al. |
| 7,127,300 B2 | 10/2006 | Mazar et al. |
| 7,138,902 B2 | 11/2006 | Menard |
| 7,147,600 B2 | 12/2006 | Bardy |
| 7,171,166 B2 | 1/2007 | Ng et al. |
| 7,171,274 B2 | 1/2007 | Starkweather et al. |
| 7,181,505 B2 | 2/2007 | Haller et al. |
| 7,215,991 B2 | 5/2007 | Besson et al. |
| 7,218,969 B2 | 5/2007 | Vallapureddy et al. |
| 7,280,872 B1 | 10/2007 | Mosesov et al. |
| 7,336,991 B2 | 2/2008 | Yanagihara et al. |
| 7,347,819 B2 | 3/2008 | Lebel et al. |
| 7,359,753 B2 | 4/2008 | Bange et al. |
| 7,382,247 B2 | 6/2008 | Welch et al. |
| 7,395,117 B2 | 7/2008 | Mazar et al. |
| 7,399,277 B2 | 7/2008 | Saidara et al. |
| 7,457,669 B2 | 11/2008 | Katoozi et al. |
| 2001/0000959 A1 | 5/2001 | Campana, Jr. |
| 2001/0051766 A1 | 12/2001 | Gazdzinski |
| 2002/0002326 A1 | 1/2002 | Causey, III et al. |
| 2002/0087203 A1 | 7/2002 | Schmitt et al. |
| 2003/0161411 A1 | 8/2003 | McCorkle et al. |
| 2003/0203721 A1 | 10/2003 | Berezdivin et al. |
| 2004/0059391 A1 | 3/2004 | Sweeney et al. |
| 2004/0171921 A1 | 9/2004 | Say |
| 2004/0176033 A1 | 9/2004 | Tamaki et al. |
| 2005/0075696 A1 | 4/2005 | Forsberg |
| 2005/0245795 A1 | 11/2005 | Goode, Jr. |
| 2005/0267650 A1 | 12/2005 | Carpenter et al. |
| 2007/0123290 A1 | 5/2007 | Stenmark |
| 2008/0177154 A1 | 7/2008 | Hansen et al. |

FOREIGN PATENT DOCUMENTS

| | | |
|---|---|---|
| JP | 2008-508029 | 3/2008 |
| RU | 2006145962 | 7/2008 |
| RU | 2319311 | 10/2008 |
| WO | 2004061420 | 7/2004 |

OTHER PUBLICATIONS

Carrol R et al: Continua: An Interoperable Personal Healthcare Ecosystem:, IEEE Pervasive Computing, IEEE Service Center, Los Alamitos, CA, US, vol. 6 No. 4, Oct. 1, 2007 pp. 90-94.

Fritz F. Klein and David A. Davis; A Low-Powered 4-Channel Physiological Radio Telemetry System for Use in Surgical Patient Monitoring; Nov. 1976; IEEE Transactions on Biomedical Engineering, vol. BME-23, No. 6.

Adina Matache; Encoding/Decoding Reed Solomon Codes; Oct. 20, 1996; Department of Electrical Engineering, University of Washington.

International Telecommunication Union, ITU-T Recommendation I.432.1, B-ISDN User-Network Interface—Physical Layer Specification:General Characteristics; article; Feb. 1999.

Lee Freitag, Milica Stojanovic, Sandipa Singh, and Mark Johnson; Analysis of Channel Effects on Direct-Sequence and Frequency-Hopped Spread-Spectrum Acoustic Communication; journal; Oct. 2001; IEEE Journal of Oceanic Engineering, vol. 26, No. 4.

Jie Nie; Saw Based Transmitter Design Notes; article; Aug. 20, 2003.

Adina Matache; Erasure Decoding; Oct. 20, 1996; Department of Electrical Engineering, University of Washington.

Software 780 implementing one or more innovations in command communication between wireless devices

METHOD AND SYSTEM FOR COMMUNICATION BETWEEN WIRELESS DEVICES

CROSS REFERENCE TO RELATED APPLICATIONS

The present application claims priority to U.S. Provisional Patent Application No. 61/092,717, filed Aug. 28, 2008, the entire disclosure of which is hereby incorporated by reference in its entirety.

TECHNICAL FIELD

Embodiments herein relate to the field of medical devices, and, more specifically, to communication between monitoring devices and receivers.

BACKGROUND

Existing medical monitoring devices, such as continuous blood glucose monitors, allow patients to track health conditions on a regular and continuous basis. For example, a continuous blood glucose monitor worn close to a patient's body and having sensors placed through the skin can sample blood glucose data at a constant rate and provide this data to a reporting/monitoring system for the patent to observe. The continuous nature of the data sampling provides patients with a better, more granular understanding of their condition and how it changes hour-by-hour, or even minute-by-minute.

In some existing devices, in order to provide for increased ease of use and comfort to the patient, a two part monitoring system is used. This system allows a relatively small data-gathering device to be placed close to the body and in contact with the patient. The data-gathering device then wirelessly transmits its sampled data to a separate monitoring device, such as a handheld device. This monitoring device provides easy access to the data obtained by the data-gathering device, and may also provide the ability to control operations of the data-gathering device. The use of the two devices can provide easier use than direct manipulation of the data-gathering device, as it may be inconveniently located on the body or be set up underneath clothing.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment," "embodiments," or "implementation(s)" which may each refer to one or more of the same or different embodiments/implementations. Furthermore, the terms "comprising," "including," "having," and the like, as used with respect to embodiments, are synonymous.

In various embodiments, methods, apparatuses, and systems for command communication between wireless devices are provided. In exemplary embodiments, a computing device may be endowed with one or more components of the disclosed apparatuses and/or systems and may be employed to perform one or more methods as disclosed herein.

Embodiments herein provide, in a system in which communications between two wireless devices involve frequency hopping, for the use of a dedicated command frequency for the transmission and receipt of non-data instructions. The devices utilize the dedicated frequency for acquisition and pairing of devices with each other. The devices also rely on protocols which periodically listen for activity on the frequency in order to identify commands that are being sent between a monitoring device and a data acquisition device.

The devices also utilize the dedicated frequency for operation in a flight mode, where the data acquisition device lowers the power on its radio frequency engine, or even shuts the radio frequency engine off. This is of particular use during air travel, and in particular on commercial aircraft, where regulations prohibit or curtail the use of electronic devices which transmit over radio frequencies while a user's plane is in the air. The data acquisition device is then able to listen for instructions to end the flight mode by checking the dedicated command channel. Also, when communications are interrupted or when for some other reason the data acquisition device has not received acknowledgment of its data transmissions for a period of time, the data acquisition device is able to go into a quiet mode. In this mode, the device stores its sampled data and listens for a re-pairing instruction from the monitoring device.

I. System

Figure 1:
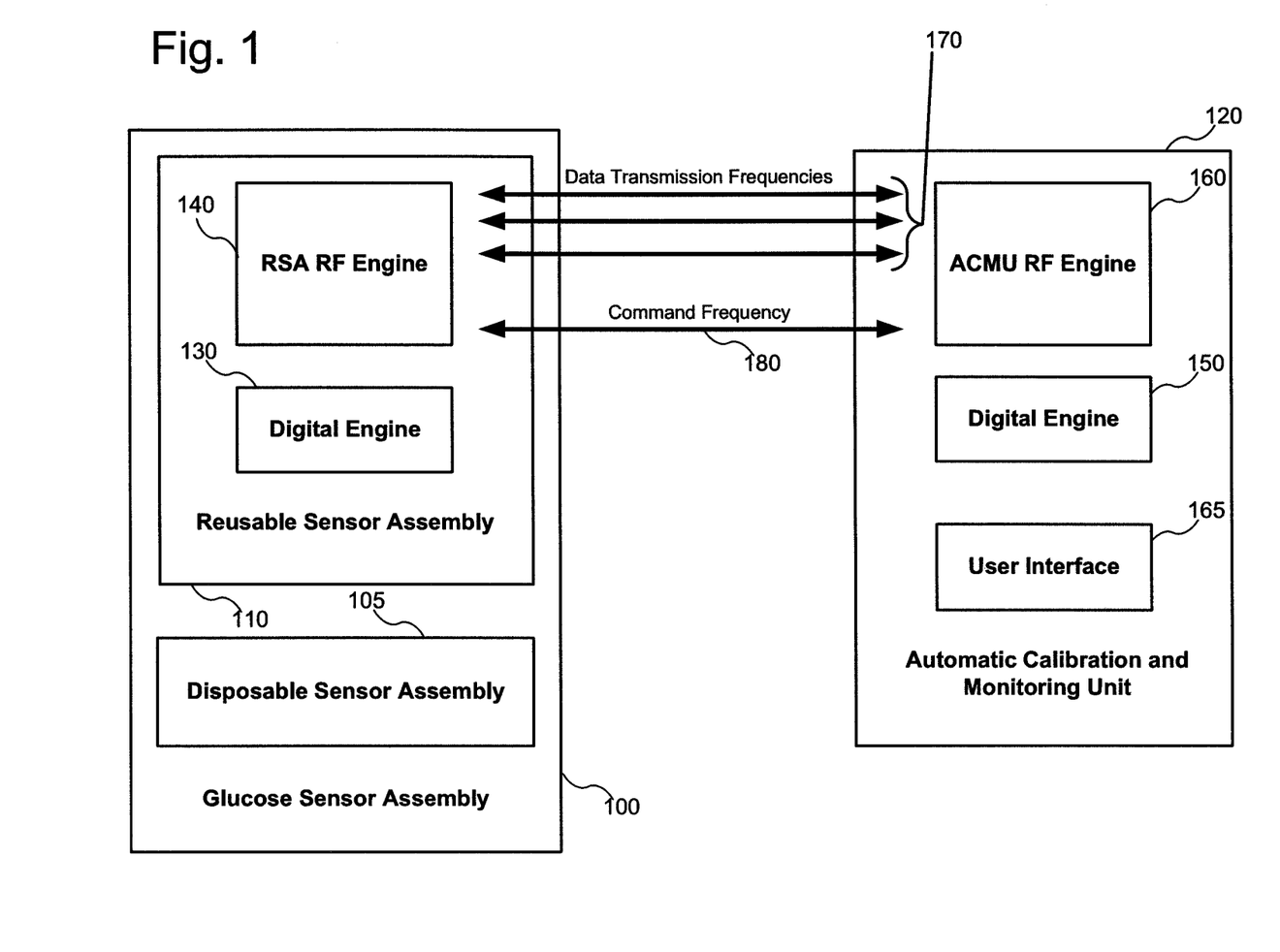
FIG. 1 is a block diagram illustrating components used in accordance with various embodiments.

FIG. 1 illustrates a block diagram of modules, components, and communications between a data acquisition device and a monitoring device. In the illustrated example, the data acquisition device is a glucose sensor assembly 100 ("GSA"), which is in communication with an automatic calibration and monitoring unit 120 ("ACMU"). While FIG. 1 illustrates these particular examples of systems using the communication techniques described herein, in alternative implementations, the techniques may be used on other medical devices, or between non-medical wireless devices.

GSA 100 comprises two parts: a disposable sensor assembly 105 ("DSA") and a reusable sensor assembly 110 ("RSA"). DSA 105 provides the measuring of a patient's health data, in this case, the DSA directly measures blood glucose levels though a sensor placed through the patient's skin or within the patient's body. RSA 110, which itself does not necessarily need to be in close contact with the patient's body, then serves to take data samples provided by DSA 105 and to record and/or transmit these samples as needed. To this end, RSA 110 comprises a digital engine 130, which contains a processor and programming for running the general operations of the RSA as well as an RSA radio frequency engine 140, which handles radio frequency communications between GSA 100 and ACMU 120. In one implementation, RSA RF engine 140 comprises a Texas Instruments CC2510 combined RF transceiver and micro-controller chip, although other implementations may make use of alternative processors.

ACMU 120 is a device for receiving and monitoring data from GSA 100 as well as for providing control commands to GSA 100. Similarly to the RSA 110 portion of GSA 100, ACMU 120 comprises a digital engine 150 and a radio frequency engine 160. As in the RSA 110, digital engine 150 provides high-level operations for ACMU 120, while ACMU RF engine 160 provides for communications with RSA 110. The ACMU also comprises a user interface 165 for controlling its operations, as well as the operations of an associated RSA.

As FIG. 1 illustrates, RSA RF engine 140 and ACMU RF engine 160 communicate via a variety of frequencies. In a typical implementation, the two RF engines, under direction from their respective digital engines, utilize a frequency hopping protocol. In this protocol, the RF engines advance, at regular intervals, through a pre-defined sequence of data transmission radio frequencies (or "channels") 170 for both their transmission and receiving communications. As long as the RF engines are relatively in sync with each other, they are able to communicate across the channels even as they are changing. While FIG. 1 illustrates an example of three channels, this is done for illustration purposes and should not be read to limit the number or choice of channels used in the techniques herein. In one implementation, frequencies for the sequence of frequencies 170 may be selected from a frequency band between 2400 MHz and 2480 MHz, though in other implementations other frequency choices may be used.

FIG. 1 also illustrates the use of a command frequency 180 which is separate from the data transmission frequencies 170. This frequency, which is typically chosen to not be in the sequence of data transmission frequencies 170, is used by RSA 110 and ACMU 120 to communicate on a dedicated channel. In particular, this command channel is used for the transmission of non-data instructions or commands from ACMU 120 to RSA 110, as well as for acknowledgments from the RSA. In one implementation, this command frequency is 2474 MHz, but other frequencies may be utilized as well.

This provides a benefit over techniques which utilize only channels from a frequency hopping sequence for all communications, because the devices may utilize the dedicated command frequency for non-data communications. However, benefits of using frequency hopping for traditional data sample transmission are maintained.

II. Communication Techniques

Figure 2:
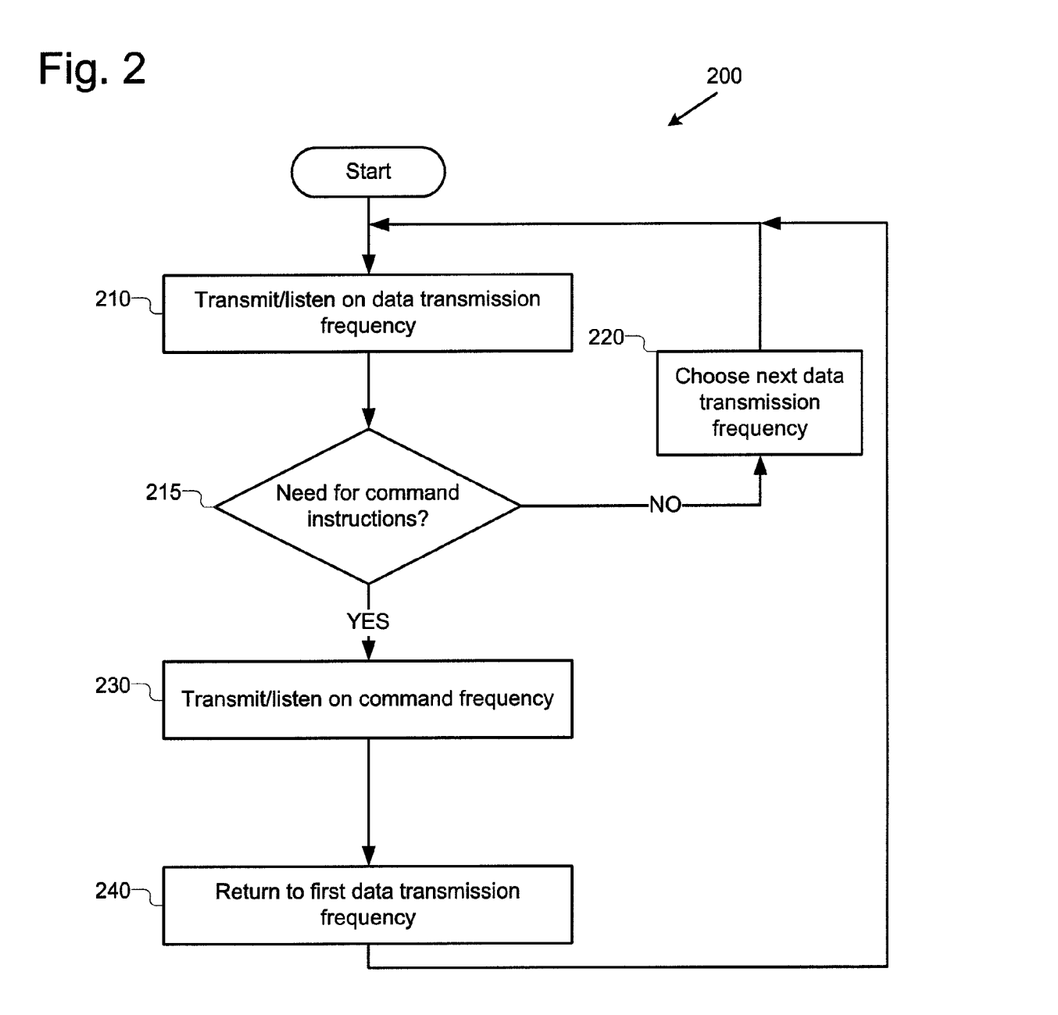
FIG. 2 is a flowchart illustrating a process for a device to operate using a dedicated command frequency in accordance with various embodiments.

FIG. 2 illustrates a flowchart of an exemplary technique 200 for utilizing a dedicated command frequency for communication between two wireless devices. The process of FIG. 2 may be performed by either RSA 110 or ACMU 120 to communicate with the other device. For the sake of illustration, the process of FIG. 2 will be described with reference to RSA 110. The process starts at block 210, where RSA 110 is transmitting data on one of the data transmission frequencies 170. Next, at decision block 215, RSA 110 determines whether it needs to listen for command instructions. Alternatively, in the case that the process of FIG. 2 is performed by ACMU 120, the ACMU would determine at block 215 if it needed to issue a command instruction. If there is no need for a command instruction, at block 220, RSA 110 chooses the next data transmission frequency from the sequence of frequencies 170, and then continues to transmit data at block 210. This looping process, when performed by both RSA 110 and ACMU 120 effectuates the frequency hopping technique described above.

RSA 110 may decide, however, that there is a need for a command instruction at decision block 215. As described in the examples below, this may happen because no acknowledgments have been received from the ACMU for a long time, because the RSA has been reset, or just because the RSA regularly listens for commands from the ACMU for a limited period of time. Alternatively, there may not be a decision made by RSA 110, but rather an interrupt or other trigger may indicate to RSA 110 that RSA 110 should switch to the command frequency to obtain some instruction/command. Whatever the reason, the process then continues to block 230 where the RSA 110 listens and transmits on the dedicated command frequency. In one implementation, this is performed by the digital engine 130 instructing the RF engine 140 to switch from listening and transmitting on one of the data transmission frequencies to listening and transmitting on the dedicated command channel. Additionally, the amount of time spent communicating on the dedicated command channel may be changed, from on the order of 10 milliseconds to many minutes, depending on the nature of the communication and/or the scenario for which the RF engine has been instructed to switch.

Finally, after communicating on the dedicated command frequency, the process continues to block 240, where RSA 110, by again switching the frequency used by RSA RF engine 140, returns to the first data transmission frequency in sequence 170. The process then returns to block 210, where data is transmitted and the entire process repeats.

III. Example Uses of Command Frequency

Figure 3:
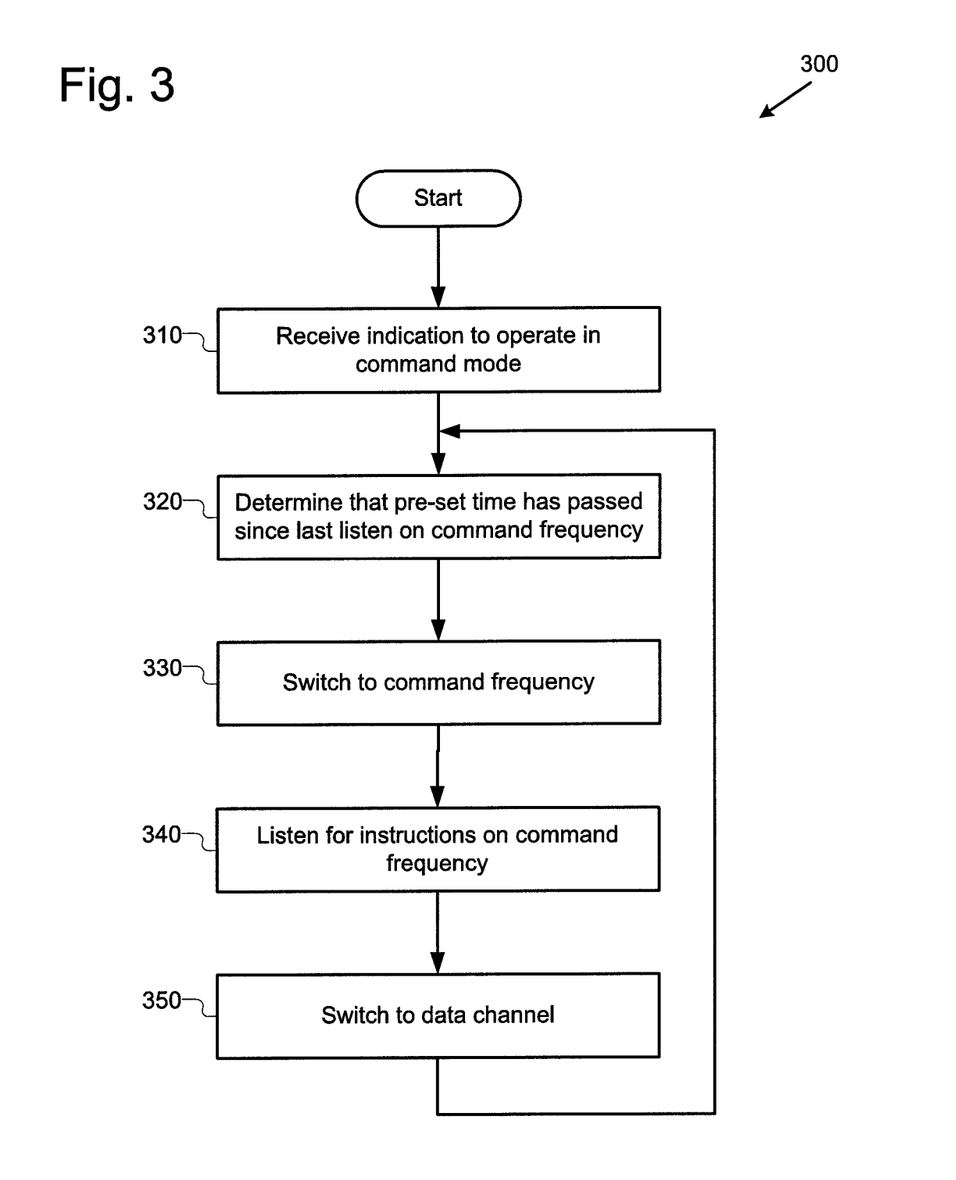
FIG. 3 is a flowchart illustrating a process for a device operating in a command mode in accordance with various embodiments.

FIG. 3 illustrates a flowchart of an exemplary technique 300 for operating in a command mode. Again, for the purposes of illustration, the process of FIG. 3 is described with reference to the RSA 110. The process begins at block 310, where the RSA 110 is indicated to operate in command mode. Typically, the RSA may utilize command mode upon power up or when reset, in order that it may find an ACMU to pair with. Next, at block 320, the RSA determines that a pre-set amount of time has passed since the last time it has listened on the command frequency. The step may be skipped, for example upon power up or reset. In one implementation, RSA 110 is configured to listen on the dedicated command frequency once every 60 seconds. The RSA may also be configured to randomly choose a time within each 60 seconds at which to listen to the command channel. This way, even though the RSA regularly listens every 60 seconds, it is unlikely to be listening, and therefore responding, to instructions at the same time as another nearby RSA. This technique reduces the likelihood of interference between two nearby RSAs, if both are in command mode.

After the determination that it is time to listen on the command channel, at block 330, RSA 110 switches to operating on the command frequency. As above, this may involve instructing the RSA RF engine to switch. Then, at block 340, the RSA listens for instructions on the command frequency. In the instant case, where listening on the command channel is done regularly, the RSA may only listen on the command channel for a short period of time, for instance 10 milliseconds. By being open for even a brief period of time, but at a regular interval, the ACMU can trust that, if it needs to send a command to the RSA, the RSA will be listening. Thus, in one implementation, when the RSA is in command mode, while the ACMU will receive an acknowledgement from the RSA when the RSA receives the ACMU's command, the ACMU does not know when the RSA will receive its commands. The ACMU therefore repeats each command it generates for at least one of the pre-set amounts of time used by the RSA (such as 60 seconds, in the example above). Thus, at some point during which the ACMU is repeating its command, an RSA within range should be listening and be able to receive the command. The process then continues to block 350, where RSA switches back to a data channel. The process then repeats at block 320, where the RSA waits until the next time it is to listen for an instruction. In one implementation (not illustrated), if the RSA does not receive a command from the ACMU within a set period of time (for example 30 minutes), the RSA will cease operation in command mode and, optionally, go into a low power mode, in order to save battery resources.

In an embodiment, the ACMU may issue two commands, Inquire and Pair, in order to effect a pairing between it and an RSA. As discussed above, the ACMU may repeat each for a period of time such as 60 seconds in order that the command may be heard by the RSA(s) with which it is communicating or attempting to pair. The Inquire command instructs each RSA, when that RSA has heard the command, to transmit an acknowledge packet which identifies the RSA. In this manner, after waiting and receiving replies, the ACMU may then generate (and display) a list of GSAs for a user to select from for pairing. The Pair command, which may be used after the Inquire command or may be used on its own, is sent as a packet containing the identity of a specific RSA, and instructs the RSA to pair with the ACMU. The ACMU, after receiving a reply from the specific RSA it identified, can then know it is paired with the RSA and begin to receive data samples transmitted from the RSA.

Alternatively, rather than controlling acquisition from the ACMU, the RSA may repeatedly send out data packets which identify the RSA, while the ACMU operates in a command mode to receive these packets. The ACMU may then list available GSAs to a user, who can select which GSA to pair with. Pairing may then proceed according to known techniques.

Figure 4:
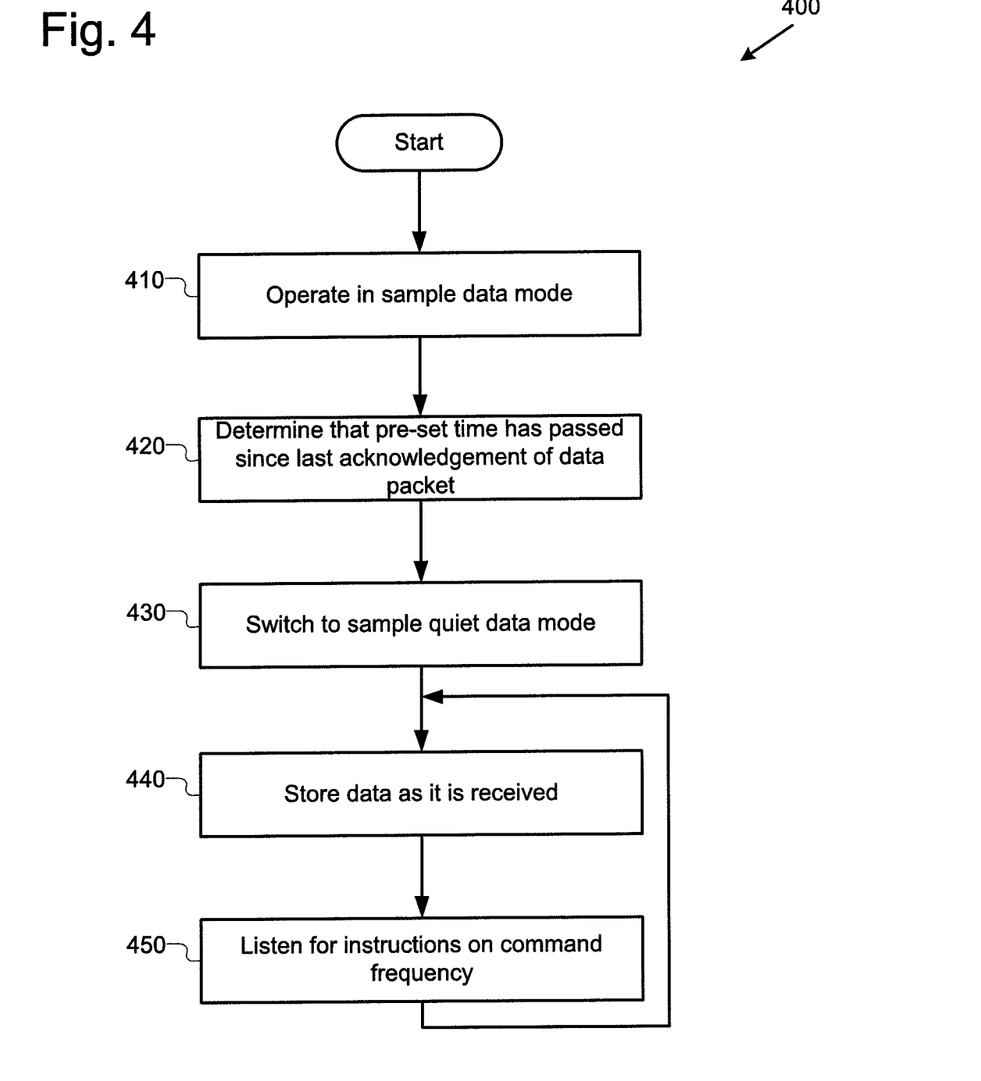
FIG. 4 is a flowchart illustrating a process for a device operating in a command mode to reacquire a link between devices in accordance with various embodiments.

FIG. 4 is a flowchart illustrating an exemplary technique 400 for an RSA operating in a quiet data mode. The process of FIG. 4 may be performed in a scenario where the ACMU has had difficulty responding to data samples sent by the RSA, such as heavy interference or the unavailability of the ACMU. The process begins at block 410, where RSA 110 is operating in sample data mode. As described above, while in this mode, the RSA may utilize frequency hopping while transmitting its data to the ACMU. Next, at block 420, the RSA determines that a pre-set time has passed since it has received an acknowledgement of a data packet it has sent. As an example, in one implementation, this period may be 90 minutes. After this time, if no acknowledgments have been received by the ACMU, the RSA switches to sample quiet data mode.

Sample quiet data mode is utilized when it may be assumed that communications are not being properly received by the ACMU. Thus, in this mode, the RSA will store data samples, rather than transmit them out, and will periodically listen for instructions on the command frequency. At block 440, then, the RSA stores data as it is received from DSA 105. Next, at block 450, the RSA listens for instructions on the command frequency. Just as in the command mode described above, the RSA may listen only for brief periods of time and at regular intervals. Hence, in one implementation, the RSA listens on the command frequency once every 60 seconds for 10 milliseconds. In yet another implementation, at block 450 the RSA is listening on the command frequency for a command to reacquire the ACMU. The process then repeats to block 440, where more data samples are stored, until the RSA receives a command to exit sample quiet data mode, at which point the process ends (not illustrated).

In an alternative implementation, a variation on the sample quiet data mode described above may also be used based on a number of unacknowledged data transmissions from the RSA. In this case, the RSA may, after not receiving an acknowledgement of a data packet, re-transmit the data packet to the ACMU and wait for a response. If, after two re-tries, no acknowledgement is received, the RSA briefly enters sample data quiet mode for 10 milliseconds, during which it listens on the command frequency to determine if a command is being sent from the ACMU.

Figure 5:
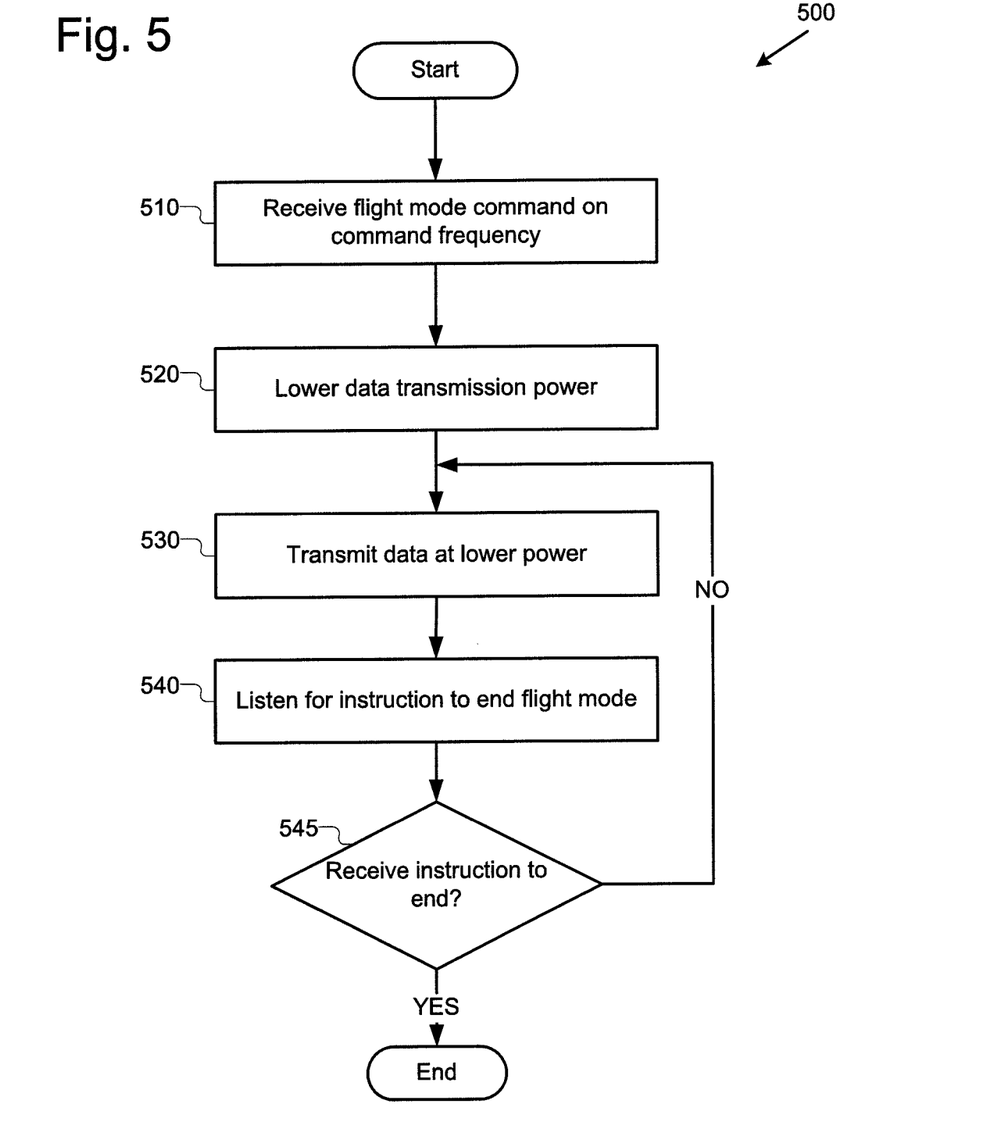
FIG. 5 is a flowchart illustrating a process for a device operating in a flight mode in accordance with various embodiments.

FIG. 5 is a flowchart illustrating an exemplary technique 500 for an RSA operating in a flight mode. The flight mode is typically chosen when the system is being used in an airplane during flight when traditional transmission power may be feared to interfere with flight systems. By operating at a reduced power, or at no transmission power at all, the flight mode allows GSA 100 to continue to sample blood glucose levels during flight and to correctly re-pair at the end of the flight without requiring direct manipulation of RSA 110. The process begins at block 510, where the RSA receives a command to operate in flight mode. While this may be through direct activation of the RSA, this is less desirable than the receipt of a command from the ACMU due, for example, to the relative inaccessibility of the RSA. Such a command may be sent to the RSA during command mode, or may be included in an acknowledgment sent after receipt of a data packet transmitted from the RSA.

The process continues at block 520, where the RSA instructs its RF engine to lower its transmitting power. In one implementation, the RF engine is instructed to lower the transmitting power to comply with FAA regulations for approved Medical Personal Electronic Devices such as those specified in RTCA/DO-160E section 21 category M. The ACMU will similarly lower its transmitting power for acknowledging packets.

Next, at block 540, the RSA will listen, for example on the command frequency for an instruction to end flight mode. In another implementation, when the RSA is configured to transmit at a low, but non-zero, power, the RSA may listen for an instruction to end that is embedded by the ACMU in an acknowledge packet. The process then continues to block 545, where the RSA determines if it has received an instruction to end flight mode. If not, the process repeats at block 530 where more low-power data transmissions are sent. If instead the instruction to end has been received, the process then ends flight mode.

In another implementation, not illustrated, the RSA lowers its transmission power completely to zero. In this implementation, instead of transmitting data during flight mode at block 530, the RSA instead stores data samples in its internal memory for the duration of the flight mode. Then, at block 540, it listens periodically for an instruction to end flight mode on the dedicated command frequency. As discussed above, this instruction may be repeated for a period of time by the ACMU until the RSA receives, processes, and acknowledges the instruction.

Figure 6:
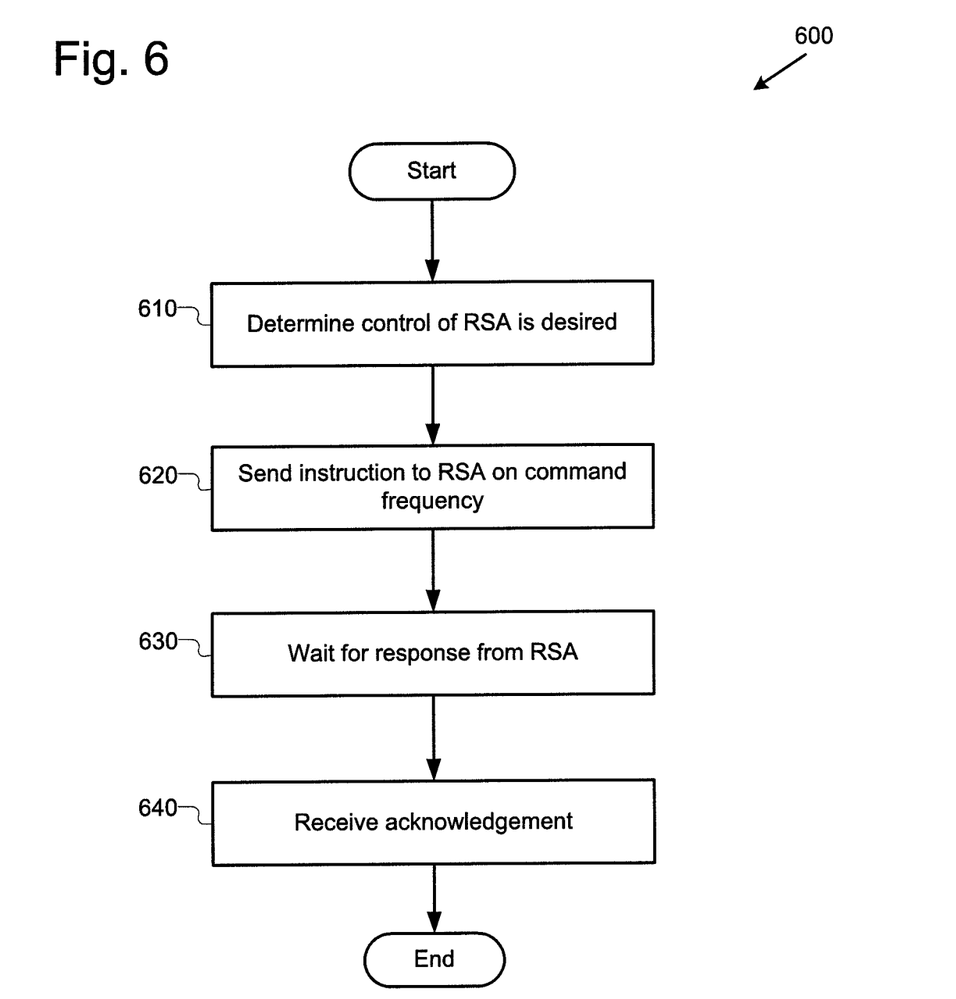
FIG. 6 is a flowchart illustrating a process for a monitoring device to communicate with a data-gathering device in accordance with various embodiments.

FIG. 6 is a flowchart illustrating an exemplary process 600 for an ACMU communicating with an RSA via the dedicated command frequency. The process begins at block 610, where the ACMU determines that control of the RSA is desired. For example, the ACMU may receive a user command through the user interface 165 or may determine that a re-pairing command needs to be sent because communications have failed between the two devices.

Next, at block 620, the ACMU sends a command to the RSA on the dedicated command frequency 180. As described above, in one implementation, the ACMU will repeatedly send the command for a pre-determined period of time because it cannot assume the RSA is listening at the initial time the command is sent; for example the ACMU may send the instruction repeatedly for 60 seconds so that at at least one point during the 60 seconds the RSA will be listening. Next, at blocks 630 and 640, the ACMU waits for a response from the RSA and receives an acknowledgment. In another implementation, the acknowledgement may not be sent, but instead the ACMU will assume that the instruction was received because it was sent for a long enough period. The process then ends.

IV. Computing Environment

Figure 7:
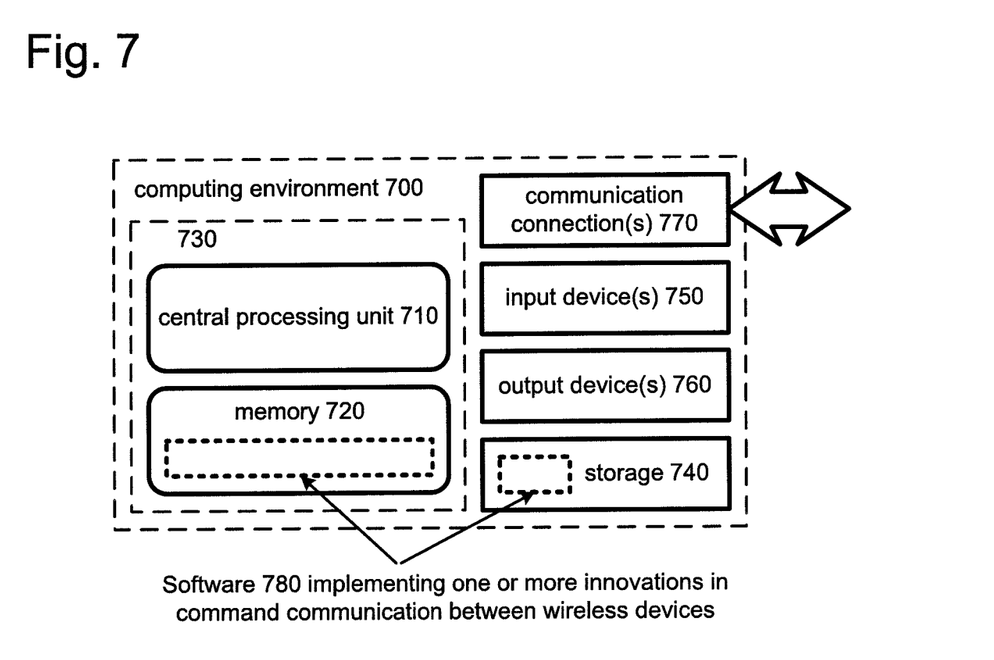
FIG. 7 is a block diagram illustrating a computing environment for use to practice various embodiments.

FIG. 7 illustrates a generalized example of a suitable computing environment 700 in which several of the described embodiments may be implemented. The computing environment 700 is not intended to suggest any limitation as to scope of use or functionality, as the techniques and tools may be implemented in diverse general-purpose or special-purpose computing environments such as personal computers, consumer electronic devices, and the like.

With reference to FIG. 7, the computing environment 700 includes at least one CPU 710 and associated memory 720. In FIG. 7, this most basic configuration 730 is included within a dashed line. The processing unit 710 executes computer-executable instructions and may be a real or a virtual processor. In a multi-processing system, multiple processing units (not illustrated) execute computer-executable instructions to increase processing power. The memory 720 may be volatile memory (e.g., registers, cache, RAM), non-volatile memory (e.g., ROM, flash memory, etc.), or some combination of the two. The memory 720 stores software 780 for implementing one or more of the communication innovations described herein.

A computing environment may have additional features. For example, the computing environment 700 includes storage 740, one or more input devices 750, one or more output devices 760, and one or more communication connections 770. An interconnection mechanism (not shown) such as a bus, controller, or network interconnects the components of the computing environment 700. Operating system software (not shown) may provide an operating environment for other software executing in the computing environment 700, and coordinates activities of the components of the computing environment 700.

The storage 740 may be removable or non-removable, and includes magnetic disks, CD-ROMs, DVDs, flash drives, solid state drives, or any other medium which can be used to store information and which can be accessed within the computing environment 700. The storage 740 stores instructions for the software 780.

The input device(s) 750 may be a touch input device such as a keyboard, mouse, pen, or trackball, a voice input device, a scanning device, a finger- or stylus-enabled touchpad, or another device that provides input to the computing environment 700. The output device(s) 760 may be a display (e.g., LCD, OLED, or CRT monitor, display screen, or the like), printer, speaker, CD- or DVD-writer, or another device that provides output from the computing environment 700.

The communication connection(s) 770 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

The techniques and tools can be described in the general context of computer-readable media. Computer-readable media are any available media that can be accessed within a computing environment. By way of example, and not limitation, with the computing environment 700, computer-readable media include memory 720, computer-readable storage media 740 (e.g., CDs, DVDs, diskettes, flash drives, removable hard drives, hard drive arrays, and solid-state drives), and combinations of any of the above.

The techniques and tools can be described in the general context of computer-executable instructions, such as those included in program modules, being executed in a computing environment on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing environment.

For the sake of presentation, the detailed description uses terms like "determine," "compute" and "categorize" to describe computer operations in a computing environment. These terms are high-level abstractions for operations performed by a computer, and should not be confused with acts performed by a human being. The actual computer operations corresponding to these terms vary depending on implementation.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method for establishing communication between a data acquisition device and a control device, the method comprising:
   transmitting one or more data packets from the data acquisition device to the control device, the transmitting being performed on one of a predetermined number of data transmission radio frequencies;
   upon a determination that non-data instructions are to be received by the data acquisition device, listening for the non-data instructions on a command radio frequency, the command frequency being other than the data transmission radio frequencies; and
   communicating to the control device on the command radio frequency;
   wherein the determination that non-data instructions are to be received comprises determining that a predetermined amount of time has expired since the data acquisition device last listened for non-data instructions on the command radio frequency.

2. The method of claim 1, wherein the listening for the non-data instructions on a command radio frequency comprises listening for a predetermined amount of time before returning to listening on one of the predetermined number of data transmission radio frequencies.

3. The method of claim 1, wherein the data acquisition device is a medical monitoring device.

4. The method of claim 3, wherein the medical monitoring device is a continuous glucose monitor.

5. A method for establishing communication between a data acquisition device and a control device, the method comprising:
   transmitting one or more data packets from the data acquisition device to the control device, the transmitting being performed on one of a predetermined number of data transmission radio frequencies;
   upon a determination that non-data instructions are to be received by the data acquisition device, listening for the non-data instructions on a command radio frequency, the command frequency being other than the data transmission radio frequencies, and
   communicating to the control device on the command radio frequency;
   wherein the determination that non-data instructions are to be received comprises determining that a predetermined number of data packets have gone unacknowledged by the control device.

6. The method of claim 5, wherein the method further comprises, after determining that a predetermined number of data packets have gone unacknowledged by the control device, operating in a quiet mode by recording and storing data until an acquisition command is received via the command radio frequency.

7. The method of claim 5, wherein the data acquisition device is a medical monitoring device.

8. The method of claim 7, wherein the medical monitoring device is a continuous glucose monitor.

9. A method for establishing communication between a data acquisition device and a control device, the method comprising:
   transmitting one or more data packets from the data acquisition device to the control device, the transmitting being performed on one of a predetermined number of data transmission radio frequencies;
   upon a determination that non-data instructions are to be received by the data acquisition device, listening for the non-data instructions on a command radio frequency, the command frequency being other than the data transmission radio frequencies; and
   communicating to the control device on the command radio frequency;
   wherein the determination that non-data instructions are to be received comprises receiving an instruction to operate in flight mode.

10. The method of claim 9, further comprising the data acquisition device, while in flight mode, reducing transmitting power for transmitting data packets to a level that complies with FAA regulations during flight.

11. The method of claim 9, further comprising the data acquisition device, while in flight mode, reducing transmitting power to zero.

12. The method of claim 9, wherein the data acquisition device is a medical monitoring device.

13. The method of claim 12, wherein the medical monitoring device is a continuous glucose monitor.

14. A method for controlling a data acquisition device from a control device, the data acquisition device configured to transmit data over a predetermined sequence of data transmission radio frequencies, the method comprising:
   determining that one or more instructions are to be sent to the data acquisition device; and
   transmitting the one or more instructions to the data acquisition device on a command frequency that is not in the predetermined sequence of data transmission radio frequencies; and
   receiving an acknowledgement from the data acquisition device on the command frequency, wherein:
   determining that one or more instructions are to be sent to the data acquisition device comprises receiving an indication that the data acquisition device should operate in flight mode;
   the one or more instructions comprising a command for the data acquisition device to operate in flight mode; and
   receiving an acknowledgement from the data acquisition device sent at a low power suitable for in-flight transmission.

15. The method of claim 14, wherein the data acquisition device is a medical monitoring device.

16. The method of claim 15, wherein the medical monitoring device is a continuous glucose monitor.

17. A method for controlling a data acquisition device from a control device, the data acquisition device configured to transmit data over a predetermined sequence of data transmission radio frequencies, the method comprising:

determining that one or more instructions are to be sent to the data acquisition device; and transmitting the one or more instructions to the data acquisition device on a command frequency that is not in the predetermined sequence of data transmission radio frequencies; and receiving an acknowledgement from the data acquisition device on the command frequency, wherein:

determining that one or more instructions are to be sent to the data acquisition device comprises determining that the data acquisition device should be re-paired with the control device; and the one or more instructions comprise re-pairing instructions.

18. The method of claim 17, wherein:

determining that the data acquisition device should be re-paired with the control device comprises determining that data is no longer being received from the data acquisition device.

19. The method of claim 17, wherein transmitting the one or more instructions to the data acquisition device on a command frequency comprises repeating transmission of the one or more instructions for a predetermined time period.

20. The method of claim 17, wherein the data acquisition device is a medical monitoring device.

21. The method of claim 20, wherein the medical monitoring device is a continuous glucose monitor.

22. A method for, in a medical monitoring device, adapting a radio frequency engine to communicate on a command channel, the radio frequency engine operating. in a frequency hopping mode using a set of data transmission channels during data transmission, the method comprising:

determining a command packet other than a data packet or a data packet acknowledgement to be communicated by the radio frequency engine, wherein determining a command other than a data packet or a data packet acknowledgement to be communicated by the radio frequency engine comprises the medical monitoring device being reset and the command packet identifying a re-pairing request between a data acquisition device and a receiving device; and instructing the radio frequency engine to transmit a command packet over a predetermined command channel other than channels in the set of data transmission channels.

23. The method of claim 22, wherein the medical monitoring device is the receiving device and the command packet is an instruction requesting information from the data acquisition device.

24. The method of claim 22, wherein the medical monitoring device is the data acquisition device and the command packet is a response to a pairing inquiry from a receiving device, the response identifying the data acquisition device.

25. The method of claim 22, wherein the data acquisition device is a medical monitoring device.

26. The method of claim 25, wherein the medical monitoring device is a continuous glucose monitor.

* * * * *